US008653032B2

(12) United States Patent
Rhyu et al.

(10) Patent No.: US 8,653,032 B2
(45) Date of Patent: Feb. 18, 2014

(54) PHARMACEUTICAL COMPOSITION FOR PREVENTING / TREATING TRPV1 ACTIVITY-RELATED AND INFLAMMATION-RELATED DISEASES OR CONDITIONS CONTAINING MAILLARD PEPTIDE SEPARATED FROM WELL-AGED TRADITIONAL SOY SAUCE AS ACTIVE INGREDIENT

(75) Inventors: Mee-Ra Rhyu, Sungnam-si (KR); Ah-Young Song, Cheongju-si (KR); Eun-Young Kim, Sungnam-si (KR); Seog Bae Oh, Seoul (KR); YoungJoo Lee, Seoul (KR); Won Chung Lim, Seoul (KR)

(73) Assignees: Korea Food Research Institute, Seongnam-si, Gyeonggi-do (KR); SNU R & DB Foundation, Seoul (KR)

( * ) Notice: Subject to any disclaimer, the term of this patent is extended or adjusted under 35 U.S.C. 154(b) by 0 days.

(21) Appl. No.: 13/508,482

(22) PCT Filed: Nov. 8, 2010

(86) PCT No.: PCT/KR2010/007845
§ 371 (c)(1),
(2), (4) Date: May 7, 2012

(87) PCT Pub. No.: WO2011/056033
PCT Pub. Date: May 12, 2011

(65) Prior Publication Data
US 2012/0225808 A1  Sep. 6, 2012

(30) Foreign Application Priority Data
Nov. 6, 2009  (KR) ........................ 10-2009-0106912

(51) Int. Cl.
*A61K 38/00* (2006.01)
*A61P 23/00* (2006.01)
*A61P 29/00* (2006.01)
*A61P 9/00* (2006.01)
*A61P 19/02* (2006.01)
*A61P 3/04* (2006.01)
*A61P 25/00* (2006.01)
*A61P 17/00* (2006.01)
*A61P 17/14* (2006.01)
*A61P 9/10* (2006.01)
*A61P 27/02* (2006.01)
*C07K 1/00* (2006.01)
*A23J 1/00* (2006.01)
*C07K 14/00* (2006.01)
*C07K 16/00* (2006.01)
*C07K 17/00* (2006.01)

(52) U.S. Cl.
USPC ......... 514/18.3; 514/1.1; 514/12.2; 514/16.4; 514/16.6; 514/16.8; 514/17.7; 514/18.7; 514/20.7; 514/20.8; 530/344; 530/412; 530/415; 530/417

(58) Field of Classification Search
None
See application file for complete search history.

(56) References Cited

FOREIGN PATENT DOCUMENTS

| KR | 10-2007-0106220 A | 11/2007 |
| KR | 10-2008-0089416 A | 10/2008 |
| KR | 10-2008-0096839 A | 11/2008 |

OTHER PUBLICATIONS

Ogasawara, M., et al., "Taste properties of Maillard-reaction products prepared from 1000 to 5000 Da peptide," Food Chemistry 99:600-604 (2006).*
Katsumata et al., "Effect of Maillard Reacted Peptides on Human Salt Taste and the Amiloride-Insensitive Salt Taste Receptor (TRPV1t)," Chem. Senses 33:665-680 (2008).*
Nishimura et al., "Decrease in Polyamines with Aging and Their Ingestion from Food and Drink," J.Biochem. 139:81-90 (2006).*
Ogasawara et al., "Taste properties of Maillard-reaction products prepared from 1000 to 5000 Dc peptide," Food Chem. 99:600-604 (2006).*
Roberts et al., "TRPV1 Antagonists as a Potential Treatmetn for Hyperalgesia," Recent Patents on CNS Drug Discovery 1:65-76 (2006).*
Wong et al., "Therapeutic potential of vanilloid receptor TRPV1 agonists and antagonists as analgesics: Recent advances and setbacks," Brain Res. Rev. 60:267-277 (2009).*
Katsumata, et al., "Effect of Maillard Reacted Peptides on Human Salt Taste and the Amiloride-Insensitive Salt Taste Receptor (TRPV1t)," Chem. Senses 33:665-680 (2008).*
Nishimura, et al., "Decrease in Polyamines with Aging and Their Ingestion from Food and Drink," J. Biochem. 139:81-90 (2006).*
Ogasawara, et al., "Taste properties of Maillard-reaction products prepared from 1000 to 5000 Da peptide," Food Chem. 99:600-604 (2006).*

(Continued)

*Primary Examiner* — Marcela M Cordero Garcia
*Assistant Examiner* — Thea D'Ambrosio
(74) *Attorney, Agent, or Firm* — Lucas & Mercanti, LLP

(57) ABSTRACT

Disclosed is a pharmaceutical composition for preventing or treating TRPV1 activity-related or inflammation-related, diseases or conditions, containing a Maillard peptide separated from well-aged traditional soy sauce as an active ingredient. The Maillard peptide in the present invention functions both as a TRPV1 agonist and a TRPV1 antagonist, and further functions as a TRPV1 activity modulator. Therefore, the Maillard peptide can be used for preventing or treating TRPV1 activity-related diseases such as pain, neurological diseases, urgent defecation, inflammatory bowel disease, respiratory diseases, urinary incontinence, overactive bladder, neurogenic / allergic / inflammatory skin diseases, skin, eye or mucosal irritation, hyperacusis, tinnitus, vestibular hypersensitivity, heart disease, etc. The Maillard peptide can further inhibit COX-2 activity, and therefore can be effectively used for preventing or treating inflammation-related diseases or conditions such as rheumatic fever, influenza, cold, throat pain, headaches, toothaches, sprains, neuralgia, synovitis, rheumatoid arthritis, degenerative arthropathies, gout, ankylosing spondylitis, psoriasis, dermatitis, etc.

4 Claims, 5 Drawing Sheets

(56) References Cited

OTHER PUBLICATIONS

Rhyu et al., "Effect of Maillard Peptides (MPs) on TRPV1 Variant Salt Taste Receptor (TRPV1t)," poster abstract—accessed online at http://legacy.library.ucsf.edu/tid/eti94g00/pdf on Aug. 9, 2013. 1 page.*

Katsumata, T. et al., "Effect of Maillard Reacted Peptides on Human Salt Taste and the Amiloride-Insensitive Salt Taste Receptor (TRPV1t)," Chem Sense, Sep. 2008, vol. 33, No. 7, pp. 665-680.

PCT International Search Report mailed Aug. 1, 2011 issued in connection with the corresponding PCT International Application No. PCT/KR2010/007845 (4 pages).

* cited by examiner

PHARMACEUTICAL COMPOSITION FOR PREVENTING / TREATING TRPV1 ACTIVITY-RELATED AND INFLAMMATION-RELATED DISEASES OR CONDITIONS CONTAINING MAILLARD PEPTIDE SEPARATED FROM WELL-AGED TRADITIONAL SOY SAUCE AS ACTIVE INGREDIENT

CROSS-REFERENCE TO RELATED APPLICATIONS

This application is a 371 of PCT/KR2010/007845, filed Nov. 8, 2010, which claims the benefit of Korean Patent Application No. 10-2009-0106912, filed Nov. 6, 2009, the entire contents of each of which are incorporated herein by reference.

TECHNICAL FIELD

The present invention relates to a composition for preventing or treating TRPV1 activity-related diseases or inflammation-related diseases.

BACKGROUND ART

Vanilloid receptor-1 (VR, or TRPV1 (transient receptor potential vanilloid-1)), also known as capsaicin receptors, refer to the receptors on nerve membrane which are activated by the stimulating compounds such as capsaicin receptor (8-methyl-N-vanillyl-6-nonenamide) which is the pungent ingredient of pepper. The molecular biological cloning of these receptors was reported in 1997 (Caterina et al., Nature, 1997, 389, 816-824). The receptors are non-selective cation channel consisting of 6 transmembrane domains, are known for selective influx of calcium ($Ca^{2+}$), and belong to TrP channel family.

TRPV1 is either activated or sensitized in response to simuli such as capsaicin, resiniferatoxin (RTX), heat (>43° C.), low pH, anandamide, lipid metabolites, etc., to play an important role as a molecular integrator in the bio-chemical noxious stimulus (Tominaga et al., Neuron, 1998, 21, 531-543; Hwang et al., PNAS, 2000, 97, 6155-6160). TRPV1 is highly expressed in the primary afferent sensory neuron, and reports say that this is also expressed in various other organs and tissues including bladder, kidney, lung, intestine, skin, central nervous system (CNS) and non-neuronal tissues (Mezey et al., PNAS, 2000, 97, 3655-3660; Stander et al., Exp. Dermatol. 2004, 13, 129-139; Cortright et al., BBRC, 2001, 281, 1183-1189). Further, TRPV1 proteins increase in diseases accompanied with severe pains. Activation of TRPV1 in response to endogenous/exogenous stimuli induce neurogenic inflammation by not only transmitting noxious stimuli, but also isolating neuropeptides such as P(substance P), CGRP (Calcitonin Gene-Related Peptide). To be specific, while the TRPV1 knock-out mouse react normally to noxious physical stimuli, vanilloids decrease pain reaction and esthesia to thermal stimulus, and hyperalgesia to thermal stimulus almost does not appear even in inflammatory condition (Caterina et al., Science, 2000, 288, 306-313; Davis et al., Nature, 2000, 405, 183-187; Karai et al., J. Clin. Invest., 2004, 113, 1344-1352).

As explained above, the TRPV1 knockout mouse has reduced responsiveness to heat or noxious stimulus, suggesting increased possibility of using the TRPV1 antagonist for the purpose of preventing or treating a variety of pain conditions. The recent reports indicate that capsazepine, which is the known TRPV1 antagonist, reduces hyperalgesia induced by physical stimuli in inflammatory and neuropathic pain models (Walker et al., JPET, 2003, 304, 56-62; Garcia-Martinez et al., PNAS, 2002, 99, 2374-2379). Further, when the primary afferent sensory neuron is treated with the TRPV1 agonist such as capsaicin, neuronal function is further damaged, leading into neuronal cell death. However, the TRPV1 antagonist was reported to act against the neuronal function damage and cell death (Holzer P., Pharmacological Reviews, 43, 143-201; Mezey et al., PNAS, 2000, 97, 3655-3660).

TRPV1 is known to be expressed in the sensory neuron distributed over the entire area of the gastrointestinal tract, and particularly highly expressed in the inflammatory diseases including irritable bowel syndrome and inflammatory bowel disease (Chan et al., Lancet, 2003, 361, 385-391; Yiangou et al., Lancet, 2001, 357, 1338-1339). Further, it was reported that TRPV1 activation stimulates sensory neuron to thus induce secretion of neuropeptides which are well known for playing a decisive role of inducing gastrointestinal disorder such as gastro-esophageal reflux disease (GERD) and stomach duodenal ulcer (DU) (Holzer P., Eur. J. Pharmacol., 2004, 500, 231-241; Geppetti et al., Br. J. Pharmacol., 2004, 141, 1313-1320). Accordingly, TRPV1 antagonist is expected to be effective in the prevention and treatment of the above-mentioned gastrointestinal disorders.

The efferent nerve, which expresses TRPV1, is prevalently distributed on the mucous membrane of respiratory track. The bronchial hyper-responsiveness has a very similar mechanism as the hyperalgesia, and protons and lipoxygenase (LOX) products as the endogenous ligand for TRPV1 are well known as the main cause of asthma and chronic obstructive bronchitis (Hwang et al., Curr. Opin. Pharmacol., 2002, 235-242; Spina et al., Curr. Opin. Pharmacol. 2002, 264-272). Further, the asthma-causing substance such as particulate matters including air pollutants react specifically to TRPV1, and such reaction was reported as been suppressed by capsazepine (TRPV1 antagonist) (Veronesi et al., NeuroToxicology, 2001, 22, 795-810). Accordingly, the possibility of using TRPV1 antagonist to treat respiratory diseases was suggested. Overacted bladder and urinary incontinence are caused by a variety of central/peripheral nerve impairment or damages and TRPV1 expressed in the efferent nerves and urinary bladder epithelial cells play critical role in the bladder inflammation (Birder et al., PNAS, 2001, 98, 13396-13401). Further, the TRPV1 knockout mouse is anatomically normal, but exhibits non-voiding bladder contracts compared to the low contracts of a normal mouse, thereby suggesting possible influence of TRPV1 on the function of bladder (Birder et al., Nat. Neuroscience, 2002, 5, 856-860).

Recently, some TRPV1 agonists have been developed for treatment of bladder disorders. TRPV1 is distributed not only in the primary efferent sensory neurons, but also on human epidermal keratinocytes (Denda et al., Biochem. Biophys. Res. Commun., 2001, 291, 1250-1250; Inoue et al., Biochem Biophys Res Commun., 2002, 291, 124-129), involves in various noxious stimulus transmission and pains such as skin irritations and itching, and closed related with skin diseases and disorder due to neurogenic/non-neurogenic factors such as cause of skin inflammation. The above is supported by the report which suggested that capsazepin, i.e., TRPV1 antagonist, suppresses inflammatory mediators in human skin cells (Southall et al., J. Pharmacol. Exp. Ther., 2003, 304, 217-222).

For the past few years, many research results reported different roles of TRPV1. Among these, relationship between blood flow/pressure regulation and plasmid glucose concentration regulation or type 1 diabetes etiology was reported (Inoue et al., Cir. Res., 2006, 99, 119-31; Razavi et al., Cell, 2006, 127, 1123-1135; Gram et al., Eur. J. Neurosci., 2007, 25, 213-223). Further, report says that the TRPV1 knockout mouse shows less anxiety-related behavior than a litter of normal mouse (Marsch et al., J. Neurosci., 2007, 27(4), 832-839).

Meanwhile, use of the TRPV1 agonist as pain reliever was also reported (Korean Patent No. 556157). The pain relieving effect by the TRPV1 agonist has mechanism of action based on the desensitization of capsaicin-sensitive sensory neurons. That is, in the early treatment of TRPV1 agonist, temporary pain and stimulations are induced due to influx of cation by the activation of TRPV1, but then the desensitization is induced to block pain with respect to not only the agonist itself, but also the other noxious stimuli. Using such characteristic, analogs such as capsaicin (brand name: Zostrix), olvanil, nuvanil, or resiniferatoxin are in use or developing stage as the treatment for acute pains, chronic pains, neurological pains, neurological damage, rheumatoid arthritis, urinary incontinence, or skin diseases (Wriggleworth and Walpole, 1998, Drugs of the Future, 23, 531-538). However, TRPV1 agonist has drawbacks of initial stimulant actions including pains and stimulations.

Korean Patent No. 707123 discloses 4-(methylsulfonylamino)phenyl analog as TRPV1 antagonist having strong pain relieving effect and a pharmaceutical composition containing the same. Korean Patent Publication No. 2008-67361 discloses indazole analog as TRPV1 antagonist. Korean Patent Publication No. 2009-35701 discloses benzimidazole analog as TRPV1 antagonist and a preparation method thereof. Korean Patent Publication No. 2009-90386 discloses benzimidazole as TRPV1 antagonist, a pharmacological composition containing the same, and a treatment method using the same. Korean Patent Publication No. 2009-90347 discloses 0-substituted dibenzyl urea derivative as TRPV1 antagonist. US Patent Publication No. 2005-277631 discloses substituted monocyclic heteroaryl TRPV1 ligand and use thereof for various treatments.

Meanwhile, Korean Patent No. 556157 discloses leciniferatoxin analog of simple structure as TRPV1 agonist which provides strong pain relieving effect, and a pharmaceutical composition containing the same.

Further, International Patent Publication Nos. 06-101321 and 06-101318 disclose TRPV1 modulator having biphenyl partial structure, and Korean Patent Publication No. 2009-6098 discloses tetrahydropyrimidoazepin derivative as TRPV1 modulator. However, most conventional TRPV1 agonist and antagonists are produced by organic synthesis, and no report has been made so far regarding the naturally occurring substance which provides biological stability.

Meanwhile, pain relieving effect by TRPV1 activation and roles of TRPV1 regarding inflammation has been reported. Noxious stimuli such as lipopolysaccharide (LPS), tissue plasminogen activator (TPA) or inflammatory factor accelerate immune system to excessively induce inflammatory substances such as TNF-α, IL-6, prostaglandin and nitric oxide to thus induce inflammatory diseases. COX-2(cyclooxygenase-2) is an enzyme that synthesizes prostaglandin and is the main pro-inflammatory mediator. The recent researches provide interesting facts about the role of COX-2 in the TRPV1 activation. By way of example, researchers have found that apoptosis by TRPV1 activation was dependent on COX-2 (Eichele K et al., Pharm. Res., 2008). Studies have also found that TRPV1 agonist, i.e., glyceryl nonivamide suppress COX-2 expression b LPS and production of prostaglandin through NF-κB as transcription factor (Lin Y et al., J. Pharmacol. Exp. Ther., 2007), and that expression of COX-2 and production of prostaglandin by TPA is meaningfully suppressed by the TRPV1 agonist (i.e., capsaicin) (Chen C W et al., Br. J. Pharmacol, 2003). Further, as the studies focused on TRPV1 role in the inflammatory response have been reported, TRPV1 agonist is gaining increasing attention as inflammation treatment (Helyes Z et al., Am. J. Physiol. Lung. Cell. Mol. Physiol., 2007; Huang W et al., Hypertension, 2009). Given the fact that the intracellular TRPV1 signalling is directly related with arachidonic acid homeostasis and COX-2 metabolism, it will be possible to investigate the possibility of using COX-2 regulation by food-derived protein metabolite for a novel agonist of TRPV1 channel.

Accordingly, in an effort to find a naturally-occurring substance that can regulate TRPV1 activity, the present inventor was confirmed that the Maillard peptides separated from well-aged traditional soy sauce can act both as agonist and antagonist for TRPV1 and thus used as a modulator for modulating TRPV1 activity, and additionally, based on the ability to suppress COX-2 activity, can be efficaciously used as a pharmaceutical composition for preventing or treating inflammation-related diseases including pain, neurological diseases, urgent defecation, inflammatory bowel disease, respiratory diseases, urinary incontinence, overactive bladder, neurogenic/allergic/inflammatory skin diseases, skin, eye or mucosal irritation, hyperacusis, tinnitus, vestibular hypersensitivity, heart disease, etc. In addition, the Maillard peptide of the present invention can inhibit COX-2 activity, and therefore can be effectively used as a pharmaceutical composition for preventing or treating inflammation-related diseases or conditions such as rheumatic fever, influenza, cold, throat pain, headaches, toothaches, sprains, neuralgia, synovitis, rheumatoid arthritis, degenerative arthropathies, gout, ankylosing spondylitis, psoriasis, dermatitis, etc., and completed the present invention.

DISCLOSURE

Technical Problem

An object of the present invention is to provide a pharmaceutical composition for preventing or treating TRPV1 activity-related diseases, comprising Maillard peptides separated from well-aged traditional soy sauce as an active ingredient.

Another object of the present invention is to provide a pharmaceutical composition for preventing or treating inflammation-related diseases, comprising Maillard peptides separated from well-aged traditional soy sauce as an active ingredient.

In order to achieve the above-mentioned object, the present invention provides a pharmaceutical composition for preventing or treating TRPV1 activity-related diseases comprising Maillard peptides separated from well-aged traditional soy sauce as an active ingredient, which acts both as agonist and antagonist to TRPV1 and thus acts as a modulator to modulate TRPV1 activity.

Further, the present invention provides a pharmaceutical composition for preventing or treating inflammation-related diseases, comprising Maillard peptides separated from well-aged traditional soy sauce as an active ingredient and inhibit COX-2 activity.

Advantageous Effects

Since the Maillard peptides separated from well-aged traditional soy sauce act both as agonist and antagonist to TRPV1, the Maillard peptides act as a modulator to modulate TRPV1 activity, and thus can be efficaciously used as a pharmaceutical composition for preventing or treating inflammation-related diseases including: pain, neurological diseases, urgent defecation, inflammatory bowel disease, respiratory diseases, urinary incontinence, overactive bladder, neurogenic/allergic/inflammatory skin diseases, skin, eye or mucosal irritation, hyperacusis, tinnitus, vestibular hypersensitivity, heart disease, etc. In addition, the Maillard peptide of the present invention can inhibit COX-2 activity, and therefore can be effectively used as a pharmaceutical composition for preventing or treating inflammation-related diseases or conditions such as rheumatic fever, influenza, cold, throat pain, headaches, toothaches, sprains, neuralgia, synovitis, rheumatoid arthritis, degenerative arthropathies, gout, ankylosing spondylitis, psoriasis, dermatitis, etc.

BEST MODE

Figure 1:
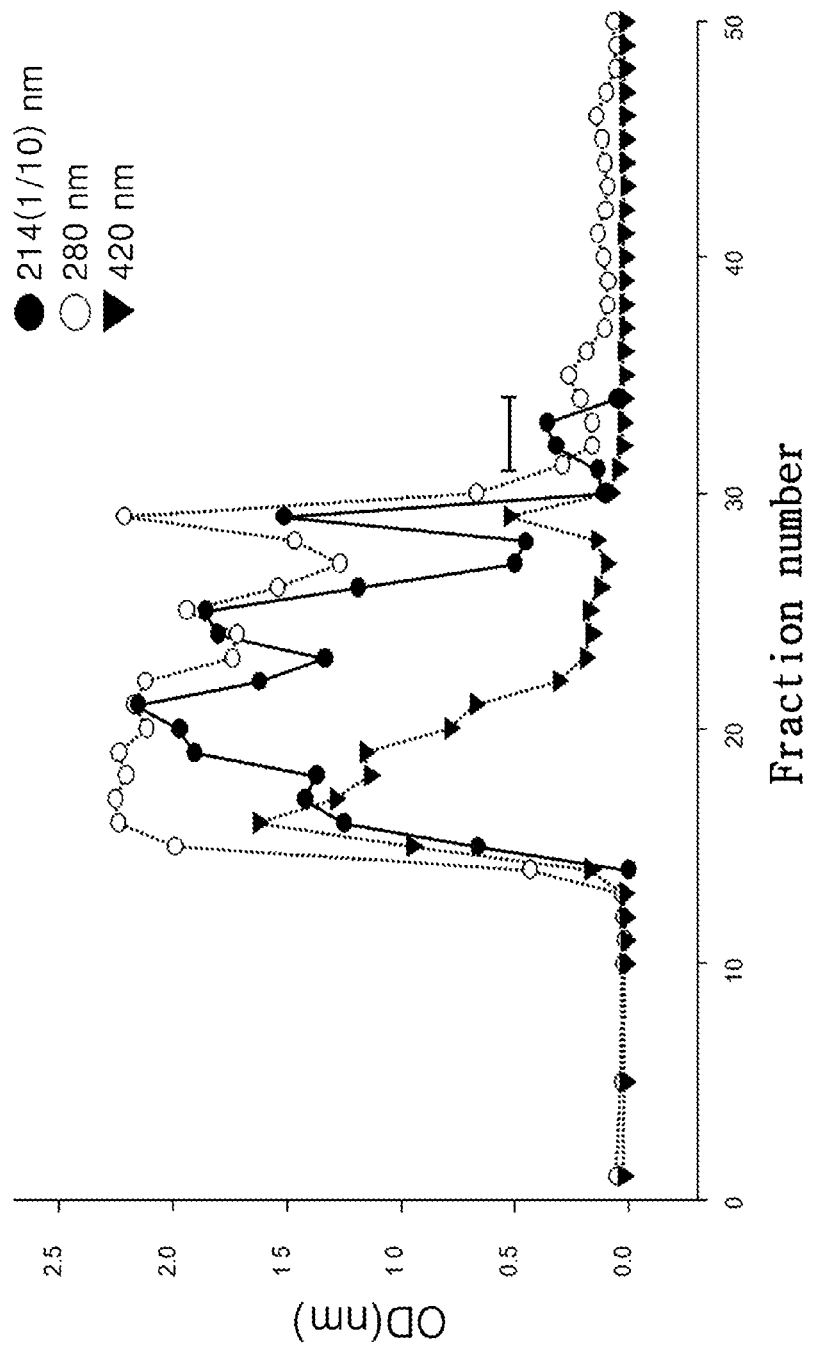
FIG. 1 is a graphical representation of light absorbance measured during isolation of Maillard peptides of Example 1 according to the present invention.

The present invention provides a pharmaceutical composition for preventing or treating TRPV1 activity-related diseases containing Maillard peptides separated from well-aged traditional soy sauce as an active ingredient.

Further, the present invention provides a method for treating TRPV1 activity-related diseases comprising administering Maillard peptides or pharmaceutically acceptable salts thereof with effective dose to a patient in need of the same.

Furthermore, the present invention provides use of said Maillard peptides or pharmaceutically acceptable salts thereof in the preparation of a medicine for treating TRPV1 activity-related diseases.

The molecular weight of the mailard peptides may preferably range from 500 to 10,000. If the molecular weight of the mailard peptides is less than 500, free amino acid, free sugar, salts may be contained and if the molecular weight of the mailard peptides is over 10,000, ingredients other than peptides such as decomposed proteins or impurities in maturing process may be contained.

The well-aged traditional soy sauce may be matured preferably for 3 or more years. If the well-aged traditional soy sauce is matured less than 3 years, the amount of generated mailard peptides is insufficient.

According to the present invention, Maillard peptides may be used for preventing or treating TRPV1 activity-related diseases by regulating TRPV1 activity.

The diseases associated with TRPV1 activity regulation may include pain, neurological diseases, diabetic peripheral neuropathy (Kamei et al., Eur. J, Pharmacol., 2001, 422, 83-86), abnormality of bowel control, irritable bowel syndrome (Chan et al., Lancet, 2003, 361, 385-391), inflammatory bowel disease (Yiangou et al., Lancet, 2001, 357, 1338-1339), gastroenteric troubles, respiratory diseases, urinary incontinence (Birder et al., Nat. Neuroscience, 2002, 5, 856-860), overactive bladder (Birder et al., PNAS, 2001, 98, 13396-13401), neurogenic/allergic/inflammatory skin diseases, epispastics, inflammation of eye or mucousal irritation (Tominaga et al., Neuron, 1998, 21, 531-543), hyperacusis, tinnitus, vestibular hypersensitivity (Balaban et al., Hear Res., 2003, 175, 165-170), heart diseases, abnormalities of growing hair, rhinitis (Seki et al., Rhinology, 2006, 44, 128-134), pancreatitis (Hutter et al., Pancreas, 2005, 30, 260-265), bladder infection (Dinis et al., J. Neurosci., 2004, 24, 11253-11263; Sculptoreanu et al., Neurosci. Lett., 2005, 381, 42-46), dysesthetic vulvodynia (Tympanidis et al., Eur. J. Pain., 2004, 8, 12-33), or mental illnesses (Marsch et al., J. Neurosci., 2007, 27(4), 832-839).

The pain may include acute pain, chronic pain, neuropathic pain, postoperative analgesia, rheumatalgia, osteoarthritis, postherpetic neuralgia, neuralgia, headache, toothache, pelvic pain, migraine, pain from bone cancer, breast pain, or visceral pain (Petersen et al., Pain, 2000, 88, 125-133; Walker et al., J. Pharmacol. Exp. Ther., 2003, 304, 56-62; Morgan et al., J. Orofac. Pain, 2005, 19, 248-260; Dinis et al., Eur. Urol., 2005, 48, 162-167; Akerman et al., Br. J. Pharmcol., 2004, 142, 1354-1360; Ghilardi et al., J. Neurosci., 2005, 25, 3126-3131; Gopinath et al., BMC Womens Health, 2005, 5, 2-9).

The neurological diseases may include HIV-related neuropathy, nerve damage, Neurodegenerative Diseases, or stroke (Park et al., Arch. Pharm. Res., 1999, 22, 432-434; Kim et al., J. Neurosci., 2005, 25(3), 662-671).

The gastroenteric troubles may include Gastro-esophageal Reflux Disease, Gastroduodenal Ulcer, or Crohn's disease (Holzer P., Eur. J. Pharmacol., 2004, 500, 231-241; Geppetti et al., Br. J. Pharmacol., 2004, 141, 1313-1320).

The respiratory diseases may include asthma, chronic obstructive pulmonary disease, or cough (Hwang et al., Curr. Opin. Pharmacol., 2002, 235-242; Spina et al. Curr. Opin. Pharmacol., 2002, 264-272; Geppetti et al., Eur. J. Pharmacol., 2006, 533, 207-214; McLeod et al., Cough, 2006, 2, 10).

The neurogenic/allergic/inflammatory skin diseases may include psoriasis, pruritus, prurigo, or skin irritation (Southall et al., J. Pharmacol. Exp. Ther., 2003, 304, 217-222).

The heart diseases may include myocardial ischemia (Scotland et al., Circ. Res., 2004, 95, 1027-1034; Pan et al., Circulation 110, 2004, 1826-1834).

The abnormalities of growing hair may include hirsutism, bromhidrosis, or alopecia (Bodo et al., Am. J. Patho., 2005, 166, 985-998; Biro et al., J. Invest. Dermatol., 2006, 1-4).

Figure 2:
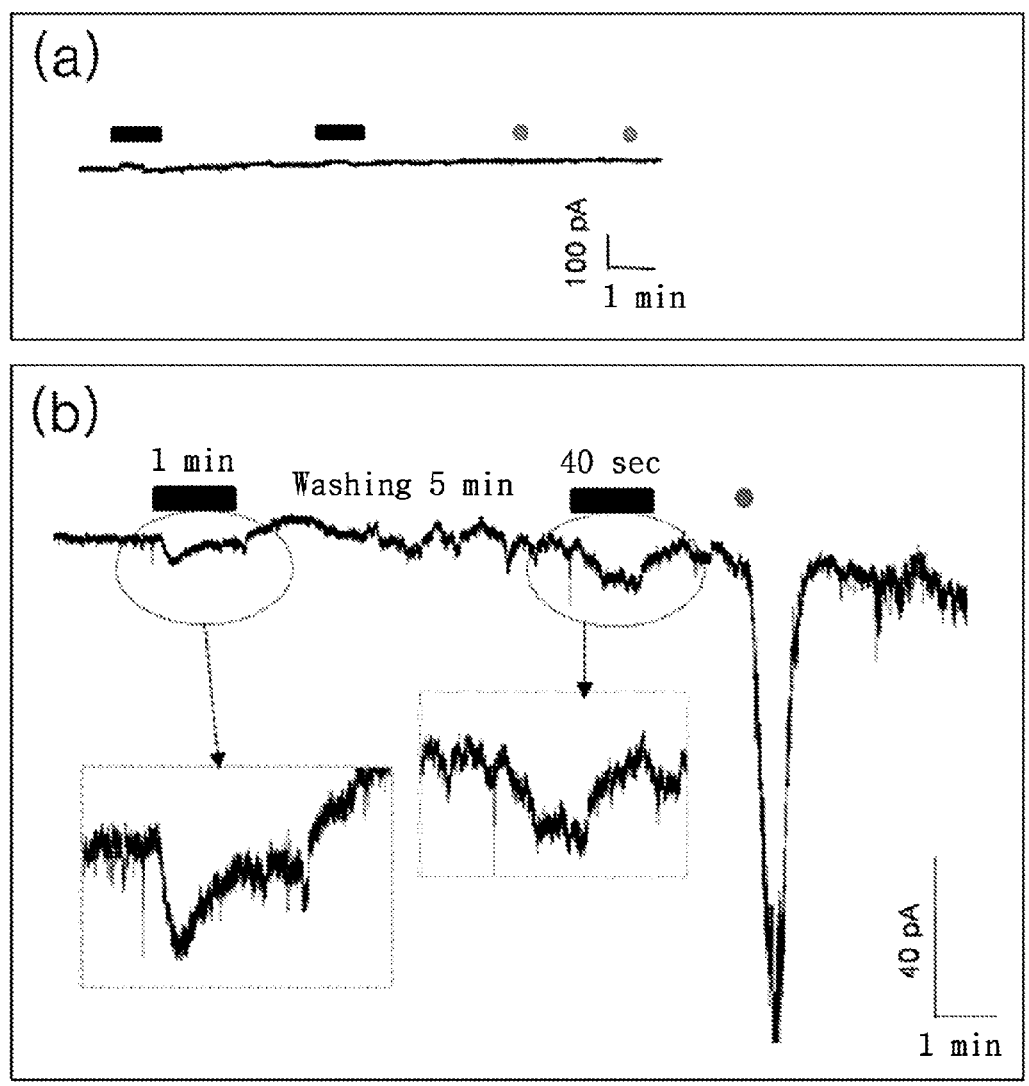
FIG. 2 is a graphical representation of measured activity of Maillard peptides according to the present invention to TRPV1, in which (a) indicates HEK 293 cells not expressing TRPV1 and (b) indicates HEK 293 cells expressing TRPV1.

According to the result of an experiment of measuring TRPV1 activity, when Maillard peptides were treated in the group expressing TRPV1, 15 pA of weak introversion current was generated, indicating TRPV1 activity (See Example 1, FIG. 2).

Also, according to the result of an experiment of measuring TRPV1 activity depending on administration time, when Maillard peptides and 100 nM of capsaicin were treated in order, 50 to 70% of current were less generated than when 100 nM of capsaicin was treated alone. Therefore, it was confirmed that Maillard peptides of the present invention act as an antagonist to inhibit TRPV1 activity (See Example 2, FIG. 3).

Accordingly, since Maillard peptides separated from the well-aged traditional soy sauce function both as TRPV1 agonist and TRPV1 antagonist, the Maillard peptides can function as a modulator to modulate TRPV1 activity, and efficaciously used as a pharmaceutical composition for preventing or treating TRPV1 activity-related diseases including pain, neurological diseases, urgent defecation, inflammatory bowel disease, respiratory diseases, urinary incontinence, overactive bladder, neurogenic/allergic/inflammatory skin diseases, skin, eye or mucosal irritation, hyperacusis, tinnitus, vestibular hypersensitivity, or heart disease.

According to the present invention, Maillard peptides may be prepared by a preparation method including:

a step of centrifuging well-aged traditional soy sauce and removing pellets (Step 1);

a step of obtaining peptide fragments with molecular weight ranging from 500 to 10,000 from the well-aged traditional soy sauce of step 1 (Step 2); and a step of obtaining Maillard peptides by performing gel filtration chromatography with the well-aged traditional soy sauce of step 2 (Step 3).

Hereinafter, each step of the present invention will be explained in greater detail.

First of all, step 1 of the present invention may be carried out to centrifuge well-aged traditional soy sauce and remove pellets therefrom.

The centrifuge may preferably be performed at 7,000~12,000 rpm, 10~20 min, and also performed preferably at 4° C. to prevent degeneration of peptides. By the centrifuge, the pellets contained in the well-aged traditional soy sauce are removed.

Next, step 2 may be carried out to obtain peptide fragments having molecular weight ranging from 500 to 10,000 from the well-aged traditional soy sauce of step 1.

The peptide fragments having molecular weight 500 to 10,000 may be obtained by filtering the well-aged traditional soy sauce of step 1 with ultrafiltration (U/F). The U/F system may take a form of fibre with open core formed therein, and the pore size thereof ranges generally from 0.1 to 0.001 μm. U/F is filtering method between micro filtration (M/F) and reverse osmosis (R/O), and particles or microorganisms (e.g. algae, colon bacillus, bacteria, etc.) except ionic substances of the solution can be removed excellently with U/F. Since the U/F provides superior fragmentation and permeability, to the method can discriminately concentrate and purify a specific substance from the mixture solution of polymer and low molecular weight substance.

A step of lyophilizing the obtained peptide fragments may be additionally performed.

In step 3, Maillard peptides may be obtained by performing gel filtration chromatography with the well-aged traditional soy sauce of step 2.

In this step, the peptide fragments powder of step 2 in ethanol and gel filtration chromatography is performed. For the gel filtration chromatography, the column filled with SEPHADEX LH-20 (Hydroxypropylated-cross-linked dextran) is used. Regarding the fragments obtained from step 2, 20% of ethanol is used as mobile phase and gel filtration chromatography is performed with SEPHADEX LH-20 column; therefore, Maillard peptides of the present invention are obtained.

In addition, the present invention provides a pharmaceutical composition for preventing or treating inflammation-related diseases or conditions, comprising Maillard peptides separated from well-aged traditional soy sauce as an active ingredient.

Also, the present invention provides a method for treating inflammation-related diseases or conditions comprising administering Maillard peptides or pharmaceutically acceptable salts thereof to a patient in need of the same.

Furthermore, in the preparation of a medicine for treating inflammation-related diseases or conditions, the present invention provides use of Maillard peptides or pharmaceutically acceptable salts thereof.

The Maillard peptides of the present invention may be used as a pharmaceutical composition for preventing or treating inflammation-related diseases or conditions by inhibiting COX-2 activity.

The inflammation-related diseases or conditions may include rheumatic fever (Revathi S, et al., J Pharm Biomed Anal., 2006, 42(2), 283-289), influenza (Lee et al., J Infect Dis., 2008, 198(4), 525-535; Carey et al., J Immunol., 2005, 175(10), 6878-6884), cold (Shiraishi Y et al., J Immunol., 2008, 180(1), 541-549), throat pain (Schachtel B P et al., J Clin Pharmacol., 2007, 47(7), 860-870), headaches (Drescher et al., Headache., 2006, 46(10), 1487-1491; O'Connor et al., Eur J Neurol., 2008, 15(1), e1), toothaches (Huber M A et al., J Am Dent Assoc., 2006, 137(4), 480-487), sprains (Islam M S et al., Br J Pharmacol., 2008, 154(4), 812-824), neuralgia (Suyama et al., Brain Res., 2004, 1010 (1-2), 144-150; Shackelford et al., J Pain., 2009, 10(6), 654-660), synovitis (Rattray et al., Haemophilia., 2006, 12(5), 514-517), arthritis (Hazewinkel et al., Res Vet Sci., 2008, 84(1), 74-79), rheumatoid arthritis (Sanghi et al., Cardiovasc Hematol Disord Drug Targets., 2006, 6(2), 85-100), degenerative arthropathies (Jean et al., Osteoarthritis Cartilage., 2007, 15(6), 638-645), gout (Villiger P M, Ther Umsch., 2004, 61(9), 563-566), ankylosing spondylitis (Croom K F, Drugs., 2009, 69(11), 1513-1532), psoriasis (Soriano E R et al., J Rheumatol., 2006, 33(7), 1422-1430), or dermatitis (Medeiros R et al., Eur J Pharmacol., 2007, 559(2-3), 227-235; Bae E A et al., Biol Pharm Bull., 2006, 29(9), 1862-1867).

According to the result of the experiment of measuring COX-2 activity inhibition effect, it was confirmed that Maillard peptides decreased TPA-induced COX-2 activity, and when Maillard peptides were administered along with SC0030 known as an existing antagonist of TRPV1, COX-2 activity induced by TPA was three times higher than when Maillard peptides were administered alone. Therefore, Maillard peptides of the present invention inhibit COX-2 activity (See Example 3, FIGS. 4 and 5).

That is, since Maillard peptides separated from well-aged traditional soy sauce inhibit COX-2 activity, the Maillard peptides may be efficaciously used as a pharmaceutical composition for preventing or treating inflammation-related diseases, such as rheumatic fever, influenza, cold, throat pain, headaches, toothaches, sprains, neuralgia, synovitis, rheumatoid arthritis, degenerative arthropathies, gout, ankylosing spondylitis, psoriasis, of dermatitis.

If the composition of the present invention is used as a medicine or medical supplies, the pharmaceutical composition containing Maillard peptides as an active ingredient may be formed into preparation for oral or parenteral administration, but not limited thereto.

For example, the preparation for oral administration may include tablets, pills, hard/soft capsules, liquid, suspensions, emulsifiers, syrup, granules, or elixirs, each including not only active ingredients, but also diluents (e.g. latos, dextrose, sucrose, mannito, sorbitol, cellulose and/or glycine) or slip modifiers (silica, talc, stearic acid and magnesium or calcium salt and/or polyethylene glycol thereof). Tablets also may contain bonding agents, such as magnesium aluminum silicate, starch paste, gelatin, methyl-cellulose, sodium carboxymethyl-cellulose and/or polyvinylpyrrolidone, and may also contain disintegrating agents such as starch, agar, alginic acid or sodium salt thereof or boiling mixture and/or absorbent, colorant, flavouring agent, or sweetenings depending on situations.

The pharmaceutical composition containing Maillard peptides as an active ingredient may be administered parenterally and the parenteral administration methods may include hypodermic injection, intravenous injection, intramuscular injection, or intra-chest injection. Also, in order to prepare dosage form for parenteral administration, Maillard peptides may be mixed along with a stabilizer or buffer in water, into solution or suspension for administration by ample or vial unit.

The composition may be sterilized and/or contained preservatives, stabilizers, water-dispersible powder or emulsifier accelerators, adjurvants such as salts and/or buffer for osmosis control, and useful substances for treatment. The composition also may be prepared by the generally-known method including mixing, granulating or coating.

If the pharmaceutical composition containing Maillard peptides as an active ingredient according to the present invention is prepared in unit for dose, 0.1 to 1,500 mg of Maillard peptides may preferably be contained in a unit as an active ingredient. The dose may be determined according to the Physician's prescription based on factors including a patient's weight, age, specific characteristics or severity of diseases. However, the dose for adult treatment is about 1 to 500 mg per day depending on the frequency and strongness of dose. For adult, about 5 to 300 mg is enough per day for divided intramuscular or intravenous administration but higher amount may be preferable for single dose depending on patients.

In order to demonstrate the substantial advantage and unexpected effect of the present invention, the present invention is carried out according to following examples, but not limited to these examples.

PREPARATION EXAMPLE 1

Preparation of Maillard Peptides

The traditional soy sauce matured for 4 years was centrifuged at 4° C., 9,000 rpm, 15 min to remove pellets thereof, and pressed at 60 psi with ultrafiltration (U/F) (Model No. 8400) of Amicon company (Beverly, Mass., USA) to separate peptide fragments. That is, the solution having peptides of molecular weight exceeding 10,000 and the solution having peptides of molecular weight under 10,000 were separated with ultrafiltration YM-10 (molecular weight cut-off 10,000 dalton) of Millipore company (Milipore Co., Bedford, Mass.). Then, the solution having over 10,000 of peptides molecular weight was removed. The solution having less than 10,000 of molecular weight was filtered with ultrafilter YC-05 (molecular weight cut-off 500 dalton) again. The solution having less than 500 of peptides molecular weight was removed and peptide fragments having 500 to 10,000 of molecular weight were obtained. The fragments were lyophilized to powder form, melted in 20% of ethanol, and chromatography was performed with SEPHADEX LH-20 column ($\Phi$1.9×150 cm). 20% of ethanol was used for elution. The absorbance of each eluted fragment was measured at 214 nm, 280 nm, 420 nm with spectrophotometer. The measured absorbance value is presented in FIG. 1. When fragments were separated under condition that the contents of a fragment was 8.4 ml, the eluted peak around No. 32 and 33 fragments were called Maillard peptides, thus No. 31, 32, 33 and 34 fragments were gathered and lyophilized. The amount of Maillard peptides recovered from 1.0 g of peptide fragments with molecular weight 500~10,000 was 0.087±0.014 mg and recovery rate was 8.7%.

EXAMPLE 1

Measuring TRPV1 Activity

In order to measure the effect of Maillard peptides according to the present invention on TRPV1 activity, the following experiment was performed with HEK 293 cells expressing TRPV1.

Human embryonic kidney cell HEK 293 (American Type Culture Collection, Manassas, Va.) was cultivated based on a manufacturer's recommendation, and temporary transformation was performed by seeding the cells on 35 mm plate and transforming, the next day, pcDNA structure of 0.4 μg rTRPV1 with Effectene transfection reagent (QIAGEN product) based on manufacturer's protocol. After 18 to 24 hours, the transformed cells were treated with trypsin, and used for whole cell recording experiment. The whole cell-current was amplified through EPC9 amplifier (HEKA). The electrode for record was made of borosilicate glass and was designed to have 5 to 7 MΩ of resistance when the standard intracellular fluid was filled therein. The normal extracellular fluid was used for the whole cell recording experiment, wherein the fluid contains 140 mM NaCl, 5 mM KCl, 2 mM CaCl2, 1 mM MgCl2, 10 mM glucose and 10 mM N-[2- hydroxyethyl] piperazine-N'-[2-ethanesulfonic acid] (N-[2-hydroxyethyl] piperazine-N'-[2-ethanesulfonic acid], HEPES) and pH level was regulated at 7.4 with NaOH. Also, record electrode solution contained 135 mM $CsCl_2$, 5 mM $MgCl_2$, 10 mM HEPES, 5 mM EGTA, 10 mM glucose and 1 mM Mg-ATP and pH level was regulated at 7.3 with CsOH. All medical solution's flow was induced by gravity (flow rate: 1 to 5 ml/min). The experiment was performed at room temperature (18 to 22° C.) and KCl agar brige was used to avoid liquid junction potential. For a control group, HEK 293 cells not expressing TRPV1 were used.

In general, cells have a potential difference with reference to the cell membrane. The cell membrane has membrane potential in stable condition and this is called the resting membrane potential (RMP). The RMP of cells is generally in the range of −60 to −70 mV and the current is not appeared across cell membranes in this state. The voltage clamp method used in Example 1 is artificial method for clamping membrane potential to control the current of inner-cell electrically by inserting record electrode into cells. The potential of cell membrane is cramped at RMP (i.e., −60 mV) and the electric current generated upon administering of drug was observed. The drug stimulating cells generate electric signal from the cells. In Preparation Example 1 of the present invention, Maillard peptides 0.2% and capsaicin 100 nM known as TRPV1 agent were used as the drug and after the drug was treated for 1 min, generated electric signals were recorded. FIG. 2 presents the result of the above-mentioned experiment, more specifically, FIG. 2(a) presents the result of measuring current of HEK 293 cells as a control which does not expressed TRPV1, and FIG. 2(b) presents the result of measuring current of HEK 293 cells expressing TRPV1.

Referring to FIG. 2(a), current was not generated when Maillard peptides of the present invention was treated in a control group in which TRPV1 was not expressed. Also, when Maillard peptides and capsaicin, known as an agent for activating TRPV1, were treated in order, current was not generated.

Moreover, referring to FIG. 2(b), when Maillard peptides were treated in the group in which TRPV1 was expressed, 15 pA of weak introversion current was generated. That is, Maillard peptides and capsaicin known as an agent for activating TRPV1 were treated in order, it was observed that 120 pA of current was generated.

Therefore, it was confirmed that Maillard peptides of the present invention act to activate TRPV1.

EXAMPLE 2

Measuring TRPV1 Activity by Administration Time

In order to measure the TRPV1 activity depending on the administration time of Maillard peptides of the present invention, experiment was performed with extracellular fluid which misses $Ca^{2+}$ for preventing TRPV1 desensitization.

Figure 3:
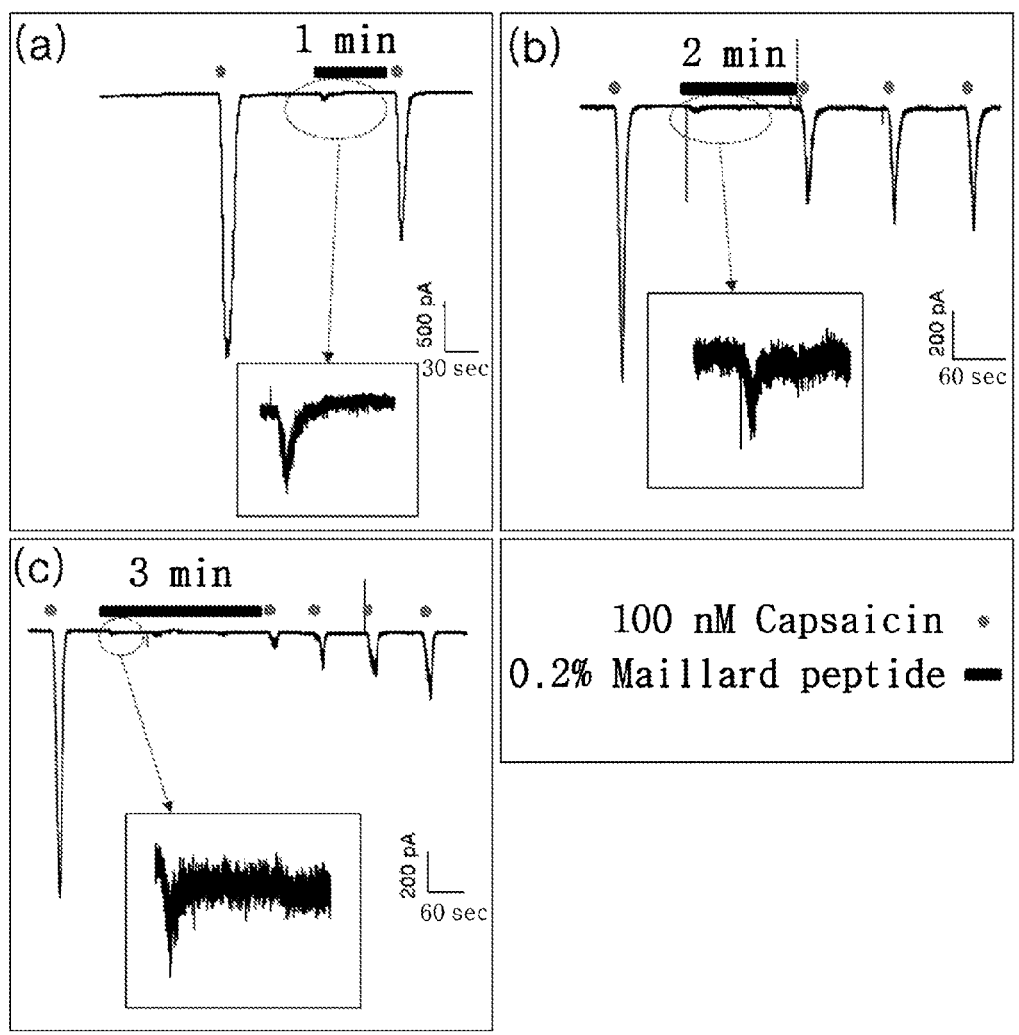
FIG. 3 is a graphical representation of activity measured regarding TRPV1 depending on administration time of Maillard peptides according to the present invention, in which (a) indicates administration for 1 min, (b) indicates administration for 2 min, and (c) indicates administration for 3 min.

In Example 2, the only difference is that the normal extracelluar fluid containing 40 mM NaCl, 5 mM KCl, 2 mM EGTA, 1 mM $MgCl_2$, 10 mM glucose and 10 mM N-[2-HYDROXYETHYL]PIPERAZINE-N'-[2- ethanesulfonic acid](N-[2-hydroxyethyl]piperazine-N'-[2-ethanesulfonic acid]; HEPES) was used instead of the extracellular fluid containing 140 mM NaCl, 5 mM KCl, 2 mM CaCl2, 1 mM MgCl2, 10 mM glucose and 10 mM N-[2-HYDROXYETHYL]PIPERAZINE-N'-[2-ethanesulfonic acid] (N-[2-hydroxyethyl]piperazine-N'-[2-ethanesulfonic acid], HEPES). Accordingly, the experiment was conducted in the same manner as that of Example 1, except for the above difference. In Example 2, 0.2% of Maillard peptides of Example 1 were treated for 1, 2, 3 min and the generated electric signals were recorded based on current. FIG. 3 presents the result of Example 2. To be specific, FIG. 3(a) presents the result of measuring current when Maillard peptides were treated for 1 min, FIG. 3(b) presents the result of measuring current when Maillard peptides were treated for 2 min, and FIG. 3 (c) presents the result of measuring the current when Maillard peptides were treated for 3 min.

According to FIG. 3(a), weak current was generated when Maillard peptides of the present invention was treated for 1 min. Also, when Maillard peptides were treated for 1 min and 100 nM of capsaicin were treated in order, weaker current was generated compared to when 100 nM of capsaicin were treated alone; therefore, Maillard peptides of the present invention decreased the current generated by capsaicin.

Moreover, according to FIGS. 3(b) and 3(c) of, when Maillard peptides were treated for 2 or 3 min, followed by treatment with 100 nM of capsaicin, the generation of current was decreased about 50 to 70% compared to when 100 nM of capsaicin was treated alone. Also, when 100 nM capsaicin was treated again after washing, generation of current was gradually increased, indicating that the current induced by capsaicin was recovering.

Therefore, it was confirmed that the Maillard peptides of the present invention act as an effective antagonist for inhibiting TRPV1 activity.

EXAMPLE 3

Measuring Inhibition Effect on COX-2 Activity

In order to measure COX-2 activity inhibition effect of Maillard peptides of the present invention, the following experiment was performed.

HEK 296 cells were cultivated in the growth medium (DMEM, 10% calf serum, 100 units/ml penicillin, 100 µg/ml streptomycin) at 37° C., atmosphere: air 95% (v/v), carbon dioxide, 5% to generate cells growing exponentially; the medium was removed, washed with PBS, and treated with trypsin to separate the cultivated cells; and the separated cells were placed in the medium containing serum to inactivate trypsin. Centrifugal filtration was performed at 200/g for 2 min to obtain cell pellets. The pellets were mixed with $5\times10^6$ cells/ml for 1 min; placed in electric shock cuvette; and pulses at room temperature with 1,500 µF, 270V with electroporator (Easyject of Equibio company) to inject plasmid (COX-2 promoter reporter gene and TRPV1 of human) within the cells. Then, the cells were placed within 10% of calf serum medium for dilution and plated within 24 well-plates. The injection efficiency of plasmid within the cells by using electroporation was converted based on activity measurement of expressed luciferase. The transformed plasmid cells were washed with PBS, and dissolution buffer (125 mM Tris pH 7.8, 10 mM CDTA, 10 mM DTT, 50% glycerol, 5% triton X-100) was added to destroy the cells and obtain supernatant liquid, and the amount (concentration) of protein was quantified with Bradford assay. Luciferase activity was measured by adding 100 µl of buffer(20 mM trysin, 1.07 mM (MgCO3) 4Mg(OH)2H20, 2.67 mM MgSO4, 0.1 mM EDTA, 33.3 mM DTT, 270 µM coenzyme A(Lithium salt), 470 µM luciferin, 530 µM ATP) and measuring light emission with Luminometer (LUMAT LB 9501/16) for 20 min. The activity of luciferase was marked as relative light unit (RLU) per 10 µg of protein.

Figure 4:
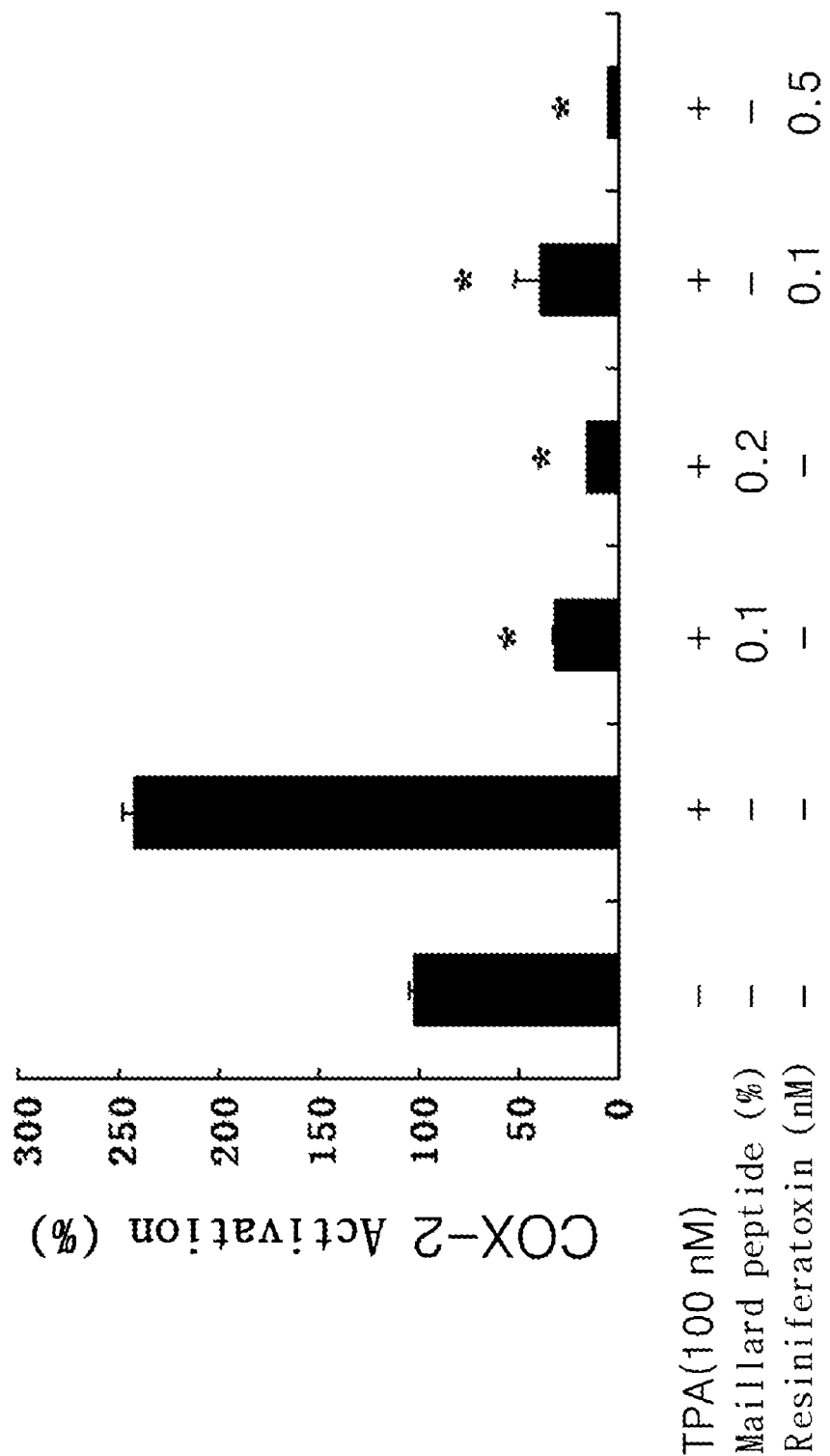
FIG. 4 is a graphical representation of COX-2 activity inhibition effect measured using Maillard peptide according to the present invention and reciniferatoxin as TRPV1 agonist.
Figure 5:
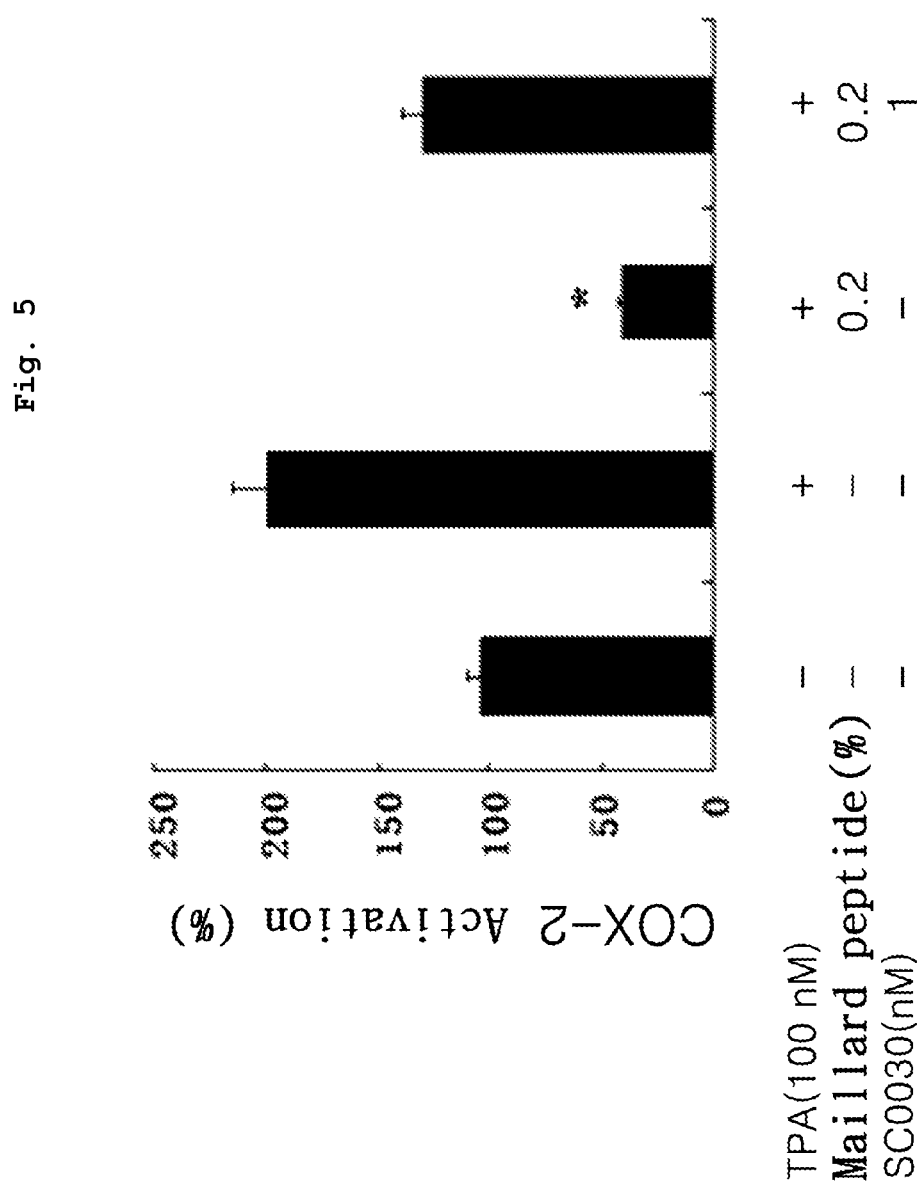
FIG. 5 is a graphical representation of COX-2 activity inhibition effect measured using Maillard peptide according to the present invention and SC0030 as TRPV1 antagonist.

Under the condition in which COX-2 was induced with TPA, Maillard peptides of Preparation Example 1 of the present invention were treated by 0.1% and 0.2% and reporter gene assay was performed. As a control group, resiniferatoxin (RTX) which is an agent of TRPV1 or SC0030 which is an antagonist of TRPV1 were used. FIGS. 4 and 5 present the result of this experiment. To be specific, FIG. 4 presents COX-2 activity level(%) when resiniferatoxin was used for a control group and FIG. 5 presents COX-2 activity level(%) when SC0030 (JYL 1421 of AstraZeneca company) was used for a control group.

According to FIG. 4, COX-2 activity induced by TPA was decreased when Maillard peptides of the present invention were administered. Also, COX-2 activity induced by TPA was decreased when resiniferatoxin known as TRPV1 agent was administered.

Referring to FIG. 5, COX-2 activity induced by TPA was decreased when Maillard peptides of the present invention were administered. Also, when Maillard peptides of the present invention and SC0030 known as an antagonist were administered at the same time, it was confirmed that COX-2 activity induced by TPA was increased three times than when Maillard peptides were administered alone and the COX-2 activity inhibition effect of Maillard peptides was inhibited due to TRPV1 antagonist.

Therefore, it was confirmed that COX-2 activity was inhibited by Maillard peptides of the present invention.

Accordingly, since Maillard peptides separated from well-aged traditional soy sauce of the present invention act both as TRPV1 agonist and antagonist, the mailard peptides may be used as the TRPV1 activity regulator to be used as a pharmaceutical composition for preventing or treating TRPV1 activity-related diseases such as pain, neurological diseases, urgent defecation, inflammatory bowel disease, respiratory diseases, urinary incontinence, overactive bladder, neurogenic/allergic/inflammatory skin diseases, skin, eye or mucosal irritation, hyperacusis, tinnitus, vestibular hypersensitivity, or heart disease. In addition, since the Maillard peptides of the present invention can inhibit COX-2 activity, these can be effectively used as a pharmaceutical composition for preventing or treating inflammation-related diseases or conditions such as rheumatic fever, influenza, cold, throat pain, headaches, toothaches, sprains, neuralgia, synovitis, rheumatoid arthritis, degenerative arthropathies, gout, ankylosing spondylitis, psoriasis, or dermatitis.

Meanwhile, Maillard peptides of the present invention may be prepared into various dosages depending on the purpose of treatment. The followings are the examples of several preparation methods containing Maillard peptides of the present invention as an active ingredient, but not limited thereto.

PREPARATION EXAMPLE 1

Preparing Powder

| | |
|---|---|
| Maillard peptides | 2 g |
| Lactose | 1 g |

Powder was prepared by mixing the above compounds and filled in airtight sachet.

PREPARATION EXAMPLE 2

Preparing Tablet

| | |
|---|---|
| Maillard peptides | 100 mg |
| Corn starch | 100 mg |
| Lactose | 100 mg |
| Magnesium Stearate | 2 mg |

Tablet was prepared by mixing the above compounds and tableting based on the known method for preparing tablet.

PREPARATION EXAMPLE 3

Preparing Capsule

| | |
|---|---|
| Maillard peptides | 100 mg |
| Lactose | 100 mg |
| Magnesium Stearate | 2 mg |

Capsule was prepared by mixing the above compounds and filling in gelatine capsule based on the known method for preparing capsule.

PREPARATION EXAMPLE 4

Preparing Injection

| | |
|---|---|
| Maillard peptides | 100 mg |
| Mannitol | 180 mg |
| Na2HPO4·2H2O | 26 mg |
| Distilled water | 2974 mg |

Injection was prepared by containing the above compounds with the described contents based on the known method for preparing injection.

The invention claimed is:

1. A method for activating TRPV1 (transient receptor potential vanilloid-1) activity in a cell, comprising:
    (i) preparing Maillard peptides by:
        (a) centrifuging well-aged traditional soy sauce and removing pellets;
        (b) obtaining a fraction containing peptide fragments from the well-aged traditional soy sauce of step (a) wherein the molecular weight of individual peptide fragments ranges from 500 to 10,000; and
        (c) purifying Maillard peptides by performing gel filtration chromatography on the fraction containing peptide fragments of step (b);
    (ii) administering a composition comprising an effective amount of a Maillard peptides produced by steps (a) through (c) to a cell expressing TRPV1; and
    (iii) measuring the activity level of TRPV 1 in the cell expressing TRPV 1.

2. The method as set forth in claim 1, wherein the well-aged traditional soy sauce used in step (a) is matured for three or more years.

3. A method for activating TRPV1 (transient receptor potential vanilloid-1) activity in a cell, comprising:
    (a) centrifuging well-aged traditional soy sauce at about 7,000 to about 12,000 RPM for about 10 to about 20 minutes and removing pellets;
    (b) using an ultrafiltration system to obtain a fraction containing peptide fragments from the well-aged traditional soy sauce of step (a) wherein the molecular weight of individual peptide fragments ranges from 500 to 10,000;
    (c) performing gel filtration chromatography on the fraction containing peptide fragments of step (b) to purify Maillard peptides;
    (d) administering a composition comprising an effective amount of a Maillard peptides produced by steps (a) through (c) to a cell expressing TRPV1; and
    (e) measuring the activity level of TRPV 1 in the cell expressing TRPV 1.

4. The method as set forth in claim 3, wherein the well-aged traditional soy sauce used in step (a) is matured for three or more years.

* * * * *